United States Patent [19]

Laas et al.

[11] Patent Number: 5,464,921
[45] Date of Patent: Nov. 7, 1995

[54] POLYISOCYANATE MIXTURES, A PROCESS FOR THEIR PRODUCTION AND THEIR USE FOR THE PRODUCTION OF POLYURETHANES

[75] Inventors: Hans-Josef Laas, Köln; Reinhard Halpaap, Odenthal; Christian Wamprecht, Neuss; Hans-Ulrich Meier-Westhues, Leverkusen; Wolfgang Schultz, Krefeld; Lothar Kahl, Bergisch Gladbach, all of Germany

[73] Assignee: Bayer Aktiengesellschaft, Leverkusen, Germany

[21] Appl. No.: 156,202

[22] Filed: Nov. 22, 1993

[30] Foreign Application Priority Data

Dec. 1, 1992 [DE] Germany ............ 42 40 330.8

[51] Int. Cl.$^6$ ............ C08G 18/10; C08G 18/32
[52] U.S. Cl. ............ 528/67; 525/452; 525/453; 528/44; 528/77; 528/85; 252/182.22
[58] Field of Search ............ 528/59, 85, 77, 528/44, 67; 252/182.22

[56] References Cited

U.S. PATENT DOCUMENTS

| | | | |
|---|---|---|---|
| 3,857,818 | 12/1974 | Frizelle | 260/77.5 TB |
| 4,159,376 | 6/1979 | Kuehn | 544/222 |
| 4,375,539 | 3/1983 | McBride et al. | 528/288 |
| 4,413,079 | 11/1983 | Disteldorf et al. | 524/169 |
| 4,463,154 | 7/1984 | Disteldorf et al. | 528/45 |
| 4,483,798 | 11/1984 | Disteldorf et al. | 260/239 |
| 4,748,242 | 5/1988 | Halpaap et al. | 544/222 |
| 4,851,531 | 7/1989 | Halpaap et al. | 544/222 |
| 4,900,800 | 2/1990 | Halpaap et al. | 528/66 |
| 4,933,416 | 6/1990 | Gillis et al. | 528/74.5 |
| 5,256,748 | 10/1993 | Vanhoye et al. | 526/261 |
| 5,288,797 | 2/1994 | Khalil et al. | 524/872 |

FOREIGN PATENT DOCUMENTS 1255660 12/1971 United Kingdom .

*Primary Examiner*—Ana L. Carrillo
*Attorney, Agent, or Firm*—Joseph C. Gil; Thomas W. Roy; Richard E. L. Henderson

[57] ABSTRACT

The present invention relates to polyisocyanate mixtures which are solid below 40° C. and liquid above 125° C. and which have a) an average isocyanate functionality of at least 2.1, b) a content of free isocyanate groups bonded to tertiary (cyclo)aliphatic carbon atoms (calculated as NCO; molecular weight=42) of 5 to 22 wt. %, c) a urethane group content calculated as —NH—CO—O—; molecular weight=59) of 2 to 30 wt. %, d) an isocyanurate group content (calculated as $C_3N_3O_3$; molecular weight=126) of 0 to 30 wt. % and e) a carboxylic acid ester group content (calculated as —CO—O—; molecular weight=44) of 0 to 25 wt. % and/or f) a carbonate group content (calculated as —O—CO—O—; molecular weight=60) of from 0 to 34 wt. % with the proviso that the total amount of ester groups e) and carbonate groups f) is at least 2 wt. %.

The present invention also relates to a process for the production of these polyisocyanate mixtures and to their use for the production of polyurethanes, in particular as the crosslinking component in heat-curable two-component polyurethane powder coatings for coating heat-resistant substrates.

1 Claim, No Drawings

POLYISOCYANATE MIXTURES, A PROCESS FOR THEIR PRODUCTION AND THEIR USE FOR THE PRODUCTION OF POLYURETHANES

BACKGROUND OF THE INVENTION

1. Field of the Invention

The present invention relates to novel, unblocked polyisocyanate mixtures suitable as crosslinking agents for powder coatings, to a process for their production and to their use for the production of polyurethanes, in particular as hardeners for polyurethane powder coatings.

2. Description of the Invention

Combinations of organic polyhydroxyl compounds and blocked polyisocyanates are valuable binders for heat-crosslinkable powder coatings. See, for example, DE-OS 2,105, 777, DE-OS 2,542,191, DE-OS 3,143,060, DE-OS 2,735,497, DE-OS 2,842,641, EP-A-0,286,799, EP-A-0, 218,040, EP-A-0,460,963, DE-OS 2,801,126, EP-A-0,403, 779, WO 91/155320 U.S. Pat. Nos. 3,857,818, 4,375,539, EP-A-0,409,745, DE-OS 2,812,252, DE-OS 2,946,085 and DE-OS 3,434,881.

Common to these prior publications is the disadvantage that, on 2O thermal crosslinking, the compounds used as blocking agents are released and escape to the environment. For ecological and occupational hygiene reasons, therefore, particular precautions have to be taken when they are processed to purify the exhaust air and/or recover the blocking agent.

An attempt to overcome this fundamental disadvantage is the use of IPDI powder coating hardeners which contain linear uretdione and urethane groups but do not contain blocking agents. These hardeners have terminal urethane, urea or free isocyanate groups (EP-A-0,045,994, EP-A-0, 045,996 and EP-A-0,045,998). Crosslinking proceeds by thermal cleavage of the uretdione groups. The disadvantage with these crosslinking agents is their strictly linear nature, which is required for the synthesis process and which does not permit the lacquer to be branched to achieve good solvent and scratch resistance, and increased hardness by varying the hardener.

EP-A-0,193,828, EP-A-0,224,165 and EP-A-0,254,152 describe certain polyisocyanates which are solid at room, temperature and contain isocyanurate and/or urethane groups and have free isocyanate groups bonded to tertiary (cyclo)aliphatic carbon atoms as the crosslinking component for PUR powder coatings. Because of the inertness of the tertiary NCO groups, these polyisocyanates may be mixed in unblocked form with OH-functional powder coating binders at temperatures above their melting point without any undesirable premature reaction occurring. In this manner, it becomes possible to produce PUR powder coatings which are stable in storage and contain no blocking agents and which crosslink at 150° to 220° C., preferably 170° to 190° C. into highly crosslinked, glossy lacquer films with good hardness, elasticity and solvent resistance.

Within the context of efforts to reduce still further solvent emissions from coating compositions, the use of powder coatings is now also being discussed for a range of applications which have previously been reserved for conventional solvent-based or water-based lacquer systems, for example, for original equipment automotive lacquer coatings. To be useful for this application, the powder coating systems must be curable at temperatures below 150° C., in particular, below 140° C., without eliminating blocking agents. This requirement:cannot be satisfied by the abovementioned polyisocyanate crosslinking agents having free tertiary bonded isocyanate groups and which do not contain blocking agent.

An object of the present invention is to provide novel, unblocked polyisocyanates which are suitable as hardeners for powder coating compositions which may be crosslinked at baking temperatures below 150° C. and which provide solvent and chemical resistant coatings having good optical and mechanical properties.

This object may be achieved with the polyisocyanate mixtures according to the invention which are described below in greater detail along with the process for their production. The polyisocyanate mixtures according to the invention are based on the surprising observation that incorporating ester and/or carbonate groups into polyisocyanates with isocyanate groups bonded on tertiary carbon atoms permits the reactivity of these isocyanate groups to be raised to such an extent that it is possible to produce powder coatings which do not contain blocking agents and which crosslink at baking temperatures well below 150° C., for example, at 120° to 140° C.

SUMMARY OF THE INVENTION

The present invention relates to polyisocyanate mixtures which are solid below 40° C. and liquid above 125° C. and which have a) an average isocyanate functionality of at least 2.1, b) a content of free isocyanate groups bonded to tertiary (cyclo)aliphatic carbon atoms (calculated as NCO; molecular weight=42) of 5 to 22 wt. %, c) a urethane group conent (calculated as —NH—CO—O—; molecular weight=59) of 2 to 30 wt. %, d) an isocyanurate group content (calculated as $C_3N_3O_3$; molecular weight=126) of 0 to 30 wt. %, e) a carboxylic acid ester group content (calculated as —CO—O; molecular weight=44) of 0 to 25 wt. % and/or f) a carbonate group content (calculated as —O—CO—O; molecular weight=60) of from 0 to 34 wt. % with the proviso that the total amount of ester groups e) and carbonate groups f) is at least 2 wt. %. The present invention also relates to a process for the production of these polyisocyanate mixtures by i) reacting at an NCO/OH equivalent ratio of 1.2:1 to 40:1 until the theoretically calculated NCO content is obtained A) diisocyanates having at least one isocyanate group bonded to a tertiary (cyclo)aliphatic carbon atom and B) optionally diisocyanaates having isocyanate groups bonded to primary and/or secondary (cyclo)aliphatic carbon atoms with C) polyhydroxyl compounds containing ester and/or carbonate groups and having an average molecular weight of 134 to 1200, D) optionally polyhydroxyl compounds which do not contain ester and carbonate groups and have a molecular weight 62 to 400, ii) optionally modifying the reaction products by the catalytic trimerization of a portion of the remaining isocyanate groups and iii) optionally separating excess, unreacted diisocyanate by thin film distillation, wherein the type and quantities of the starting materials are selected such that the products resulting from the process comply with the requirements stated above under a) to f).

The present invention further relates to the use of these polyisocyanate mixtures for the production of polyurethanes, in particular as the crosslinking component in heat-curable two-component polyurethane powder coatings for coating heat-resistant substrates.

DETAILED DESCRIPTION OF THE INVENTION

Starting compounds A) for the process according to the invention are any diisocyanates having at least one isocyanate group bonded to a tertiary (cyclo)aliphatic carbon atom. Suitable starting diisocyanates include:

A1) aliphatic diisocyanates having an NCO content of 24 to 50 wt. %, preferably 31 to 50 wt. %, which, apart from a sterically unhindered isocyanate group bonded to a primary aliphatic carbon atom, have a sterically hindered isocyanate group which is bonded to a tertiary aliphatic carbon atom, or A2) aliphatic-cycloaliphatic diisocyanates having an NCO content of 20 to 50 wt. %, preferably 30 to 48 wt. %, which, apart from a sterically unhindered isocyanate group bonded to a primary aliphatic carbon atom, have a sterically hindered isocyanate group which is bonded to a tertiary carbon atom which is part of a cycloaliphatic ring, or A3) aromatic compounds having isocyanatoalkyl substituents and an NCO content of 20 to 35 wt. %, preferably 25 to 35 wt. %, wherein both isocyanate groups are bonded to tertiary aliphatic carbon atoms.

Suitable diisocyanates A1) include those corresponding to the formula

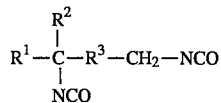

wherein $R^1$ and $^2$ represent identical or different alkyl groups having 1 to 4 carbon atoms and $R^3$ represents a divalent, optionally branch;ed, saturated aliphatic hydrocarbon residue having 2 to 9 carbon atoms.

These diisocyanates and their production are described, for example, in DE-OS 3,608,354 and DE-OS 3,620,821. Preferred diisocyanates A1) are those in which R 1 and $R^2$ each represent methyl residues. Examples include 1,4-diisocyanato-4-methyl-pentane, 1,5-diisocyanato-5-methylhexane, 1,6-diisocyanato-6-methylheptane, 1,5-diisocyanato-2,2,5-trimethylhexane and 1,7-diisocyanato-3,7-dimethyloctane.

Suitable starting diisocyanates A2) include those corresponding to the formula

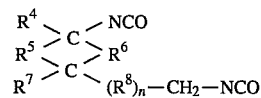

wherein $R^4$ represents an alkyl residue having 1 to 4 carbon atoms, preferably a methyl residue, $R^5$ and $R^6$ represent identical or different divalent linear or branched saturated hydrocarbon residues having 1 to 4, preferably I to 3 carbon atoms, wherein the sum of the carbon atoms in these residues is preferably 3 to 6, more preferably 4 or 5, $R^7$ represents hydrogen or an alkyl residue having 1 to 4 carbon atoms, preferably hydrogen or a methyl residue, $R^8$ represents a divalent, linear or branched, saturated aliphatic hydrocarbon residue having 1 to 4, preferably 1 to 4 carbon atoms and n represents 0 or 1.

The production of such aliphatic-cycloaliphatic diisocyanates is described, for example, in EP-A-0,153,561.

Preferred starting diisocyanates A2) include 1-isocyanato-1-methyl-4(3)-isocyanatomethylcyclohexane, which is generally present as a mixture of the 4- and 3-isocyanatomethyl isomers, 1-isocyanato-1-methyl -4-(4-isocyanatobut-2-yl)cyclohexane, 1-isocyanato-1,2,2-trimethyl-3-(2-isocyanatoethyl)cyclopentane and 1-isocyanato-1,4-(3)-dimethyl-4(3)-isocyanato-methylcyclohexane, which is generally present in the form of a 4-methyl-4-isocyanatomethyl and 3-methyl-3-isocyanatomethyl isomeric mixture. Also suitable are 1-isocyanato-l-butyl-3-(4-isocyanatobut-1-yl)cyclopentane, 1 -isocyanato-1 -ethyl-4-butyl-4-( 4-iso-cyanatobut-1-yl)cyclo-hexane and 1-isocyanato-1,2-dimethyl-3-ethyl-3-isocyanato-methylcyclopentane.

Suitable starting diisocyanates A3) include those corresponding to the formula

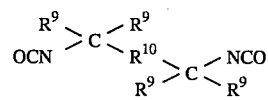

wherein $R^9$ represents an alkyl residue having 1 to 4 carbon atoms, preferably a methyl residue and $R^{10}$ represents a divalent aromatic hydrocarbon residue, selected from phenylene, biphenylene or naphthylene residues, which may optionally be substituted with halogen, methyl or methoxy groups.

These diisocyanates are known and their production is described, for example, in EP-A-0,101,832. A preferred diisocyanate A3) is 1,3- or 1,4-bis-(2 -isocyanato-prop-2-yl)benzene.

Mixtures of the diisocyanates listed by way of example under A1), A2) and A3) may also be used as starting component A) for the process according to the invention.

Preferred starting diisocyanates A) are aliphatic-cycloaliphatic diisocyanates A2). Especially preferred is 1-isocyanato-l-methyl-4(3)-isocyanatomethylcyclohexane.

Diisocyanates B) having isocyanate groups which are exclusively bonded to primary and/or secondary (cyclo)aliphatic carbon atoms may also be used in the process according to the invention. These diisocyanates preferably have a molecular weight of 140 to 400 and include 1,4-diisocyanatobutane, 1,6-diisocyanohexane, 1,5-diisocyanato-2,2-dimethylpentane, 2,2,4- or 2,4,4-trimethyl-1,6-diisocyanohexane, 1,10-diisocyanatodecane, 1,3- and 1,4-diisocyanatocyclohexane, 1-isocyanato-3,3,5-trimethyl-5-isocyanato-methylcyclohexane (isophorone diisocyanate), 4,4'-diisocyanato-dicyclohexylmethane and mixtures of these diisocyanates. A particularly preferred diisocyanate B) is 1,6-diisocyanatohexane.

If diisocyanates B) are used in the process according to the invention, they are used in quantities of up to 25 mole %, based on the total moles of starting components A) and B).

Suitable polyhydroxyl compounds C) for use in the process according to the invention have an average molecular weight, which may be calculated from functionality and OH number, of 134 to 2500, preferably 176 to 800, and an average OH functionality of 2.0 to 4.0, preferably 2.2 to 3.8. These ester alcohols or ester alcohol mixtures which are suitable as compounds C) are known and may, for example, be produced by reacting polyhydric alcohols with substoichiometric quantities of polybasic carboxylic acids (or their corresponding anhydrides esters of low molecular weight alcohols) or lactones.

Polyhydric alcohols suitable for the production of the ester alcohols include those having a molecular weight 62 to 400, such as 1,2-ethanediol, 1,2- and 1,3-propanediol, the isomeric butanediols, pentanediols, hexanediols, heptanediols and octanediols, 1,2- and 1,4-cyclohexanediol, 1,4-cyclohexane dimethanol, 4,4'-(1-methylethylidene)bi-scyclohexanol, 1,2,3-propanetriol, 1,1,1-trimethylolethane, 1,2,6-hexanediol, 1,1,1-trimethylolpropane, 2,2-bis-(hydroxymethyl)-1,3-propane-diol and 1,3,5-tris(2-hydroxyethyl)-isocyanurate.

The acids or acid derivatives used for the production of the ester alcohols may be aliphatic, cycloaliphatic, aromatic and/or heteroaromatic and may also be substituted, for example, with halogen atoms, and/or unsaturated. Examples of suitable acids include polybasic carboxylic acids having a molecular weight of 118 to 300 or their derivatives such as succinic acid, adipic acid, sebacic acid, phthalic acid, isophthalic acid, trimellitic acid, phthalic anhydride, tetrahydrophthalic acid, maleic acid, maleic anhydride, dimeric and trimeric fatty acids, terephthalic acid dimethyl ester and terephthalic acid bis-glycol ester.

Mixtures of the previously disclosed starting materials may also be used to produce the ester alcohols. It is also possible to use mixtures of various ester alcohols in the process according to the invention.

Preferred starting materials C) are the ester polyols produced in a known manner from lactones and simple polyhydric alcohols as starter molecules in ring-opening reaction.

Suitable lactones for the production of these ester polyols include β-propiolactone, γ-butyrolactone, γ- and γ-valerolactone, ε-caprolactone, 3,5,5- and 3,3,5-trimethyl-caprolactone or mixtures of these lactones. The previously disclosed polyhydric alcohols having a molecular weight 62 to 400 or mixtures of these alcohols may be used as starter molecules.

Particularly preferred polyhydroxyl compounds C) having ester groups for use in accordance with the invention are ester polyols having the required molecular weight and prepared from e-caprolactone, in particular using 1,1,1-trimethylolpropane as the starter molecule.

Further suitable starting materials C) for the process of the invention are carbonate groups containing polyhydroxy compounds known per se. Such carbonate polyols may be obtained by reacting polyvalent alcohol having a molecular weight of from 62 to 400 as exemplified hereinbefore with diaryl carbonates such diphenyl carbonate, phosgene or, preferably, cyclic carbonates such as trimethylene carbonate or 2,2-dimethyl-trimethylene carbonate (neopentyl glycol carbonate, NPC) or mixtures of such cyclic carbonates. Preferred carbonate polyols are those which are prepared from the above-mentioned polyvalent alcohols and NPC.

Further suitable starting materials C) for the process of the invention are polyols containing both ester and carbonate groups. Such alcohols may, for example, be prepared in accordance with DE-AS 1 770 245 by reacting the above exemplified polyvalent alcohols having a molecular weight of from 62 to 400 with lactones especially T-caprolactone and subsequent reaction of the resulting ester alcohols with diphenyl carbonate. A preferred method consists, however, in reacting said polyvalent alcohols with mixtures of lactones and cyclic carbonates in a ring-opening reaction. These ring-opening reactions are generally carried out in the presence of catalysts such as, for example, Lewis acids, organic tin compounds or organic titanium compounds at temperatures of from 20° to 200° C., preferably 50° to 160° C.

It is also possible to use mixtures of ester alcohols and carbonate alcohols of the kind referred to hereinbefore as polyol component C).

Polyhydroxyl compounds D) which do not contain ester or carbonate groups and have a molecular weight of 62 to 400 may optionally also be used in the process according to the invention. Examples of polyhydroxyl compounds D) include the polyhydric alcohols described above for production of the ester alcohols or mixtures of these polyhydric alcohols. Alcohols D) are used, if at all, in quantities of up to 80 wt. %, based on the total quantity of starting components C) and D). Mixtures of starting components C) and D) may be produced directly by reacting excess amounts of the previously mentioned polyhydric alcohol with substoichiometric quantities of acids, acid derivatives, diaryl carbonates or cyclic carbonates to form the mixtures of ester alcohols C) and alcohols D).

To perform the process according to the reaction, the starting diisocyanates A), optionally together with further diisocyanates B), are reacted with polyhydroxyl compounds C) containing ester groups and optionally polyhydroxyl compounds D) which do not contain ester groups, at an NCO/OH equivalent ratio of 1.2:1 to 40:1, preferably 1.4:1 to 20:1, until the theoretically calculated NCO content is reached. It is ensured by selection of the poly-hydroxyl components C) and optionally D) that the resultant polyisocyanates have an (average) NCO functionality of at least 2.1, preferably 2.1 to 5.0 and more preferably 2.2 to 4.8, unless, as described further below, there is a subsequent trimerization reaction which increases NCO functionality. In such cases, entirely dihydric compounds may be used as the polyhydroxyl components C) and D), whereas in the absence of the trimerization reaction, mixtures of difunctional and higher functional polyol components or exclusively higher functional polyol components are used.

The reaction temperature required for urethane formation in the process according to the invention is 20° to 200° C., preferably 40 to 160° C., and more preferably 40° to 120° C. The reaction is preferably performed without solvent. Known catalysts from polyurethane chemistry may be used to accelerate the urethanization reaction. Examples include tertiary amines such as triethyl-amine, pyridine, methylpyridine, benzyldimethylamine, N,N-endoethylene-piperazine, N-methylpiperidine, pentamethyldiethylenetriamine, N,N-dimethyl-aminocyclohexane, N,N'-dimethylpiperazine; or metal salts such as iron(Ill) chloride, zinc chloride, zinc-2-ethyl caproate, fin(II) ethyl caproate, dibutyltin(IV) dilaurate and molybdenum glycolate. These catalysts are optionally used in quantifies of 0.001 to 2.0 wt. %, preferably 0.01 to 0.2 wt. %, based on the total quantity of starting compounds used.

When diisocyanates A3) having two sterically hindered tertiary isocyanate groups are used, the reaction is generally followed by thin film distillation to distill of excess monomeric diisocyanate in order to obtain low monomer-containing polyisocyanate mixtures having monomer contents of less than 0.5 wt. %.

When diisocyanates A1) and A2) having one sterically hindered tertiary and one sterically unhindered primary isocyanate group are used for the process according to the invention, thin film distillation is not necessary. Provided that the NCO/OH equivalent ratio of 1.2:1 to 2:1, preferably 1.4:1 to 2:1 is maintained, low-monomer polyisocyanate mixtures having a monomer content of less than 1%, generally less than 0.5%, are directly obtained. This is due to the very much lower reactivity of the tertiary isocyanate groups compared with the primary isocyanate groups in starting diisocyanates A1) and A2) or with the primary and/or secondary isocyanate groups of diisocyanates B).

If diisocyanates A1) and/or A2), Optionally together with diisocyanates B), are reacted in an equivalent NCO/OH ratio of 2:1 to 40:1, preferably 2:1 to 20:1, with the hydroxyl components C) and optionally D), wherein the optionally used diisocyanates B) are only introduced into the reaction mixture after urethane formation from A1) and A2) together with C) and optionally D), then film distillation may be omitted in these cases too, if the sterically unhindered isocyanate groups bonded to a primary or secondary carbon atom are converted into isocyanurate groups by a subsequent trimerization reaction. The resulting polyisocyanate mixtures containing isocyanurate groups have a low monomer content of less than 1 wt. %, preferably less than 0.5 wt. %, of monomeric diisocyanate.

Suitable trimerization catalysts for the process according to the invention include those previously used for the production of isocyanurate poly-isocyanates. Examples include the phosphines described in DE-OS 1,934,763; the alkali phenolates described in GB Patents 1,391,066 or 1,386,399; the aziridine derivatives in combination with tertiary amines described in DE-OS 2,325,826; the quaternary ammonium carboxylates described in EP-OS 17,998; the quaternary ammonium phenolates having a zwitterionic structure described in U.S. Pat. No. 4,335,219; the ammonium phosphonates and phosphates described in DE-OS 3,227,608; the alkali carboxylates described in DE-OS 3,219,608; the organosilicon compounds described in EP-A-57,653, EP-A-89,297 and EP-A-187,105; the ammonium fluorides described in EP-A 339,396; and the basic alkali metal salts in combination with phase transfer catalysts described by R. Richter, P. Müller and K. Wagner, "Die Angewandte Makromolekulare Chemie", 113, 1–9 (1983).

Quaternary ammonium hydroxides having the following formula are particularly suitable as trimerization catalysts

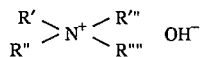

These catalysts are described in DE-OS 2,806,731 and DE-OS 2,901,479. Preferred quaternary ammonium:hydroxides are those wherein substituents R' to R"" represent identical or different alkyl or aralkyl groups having 1 to 20, preferably 1 to 7 carbon atoms, which may be substituted with hydroxyl groups; or wherein two of the substituents R' to R"" may also form, together with the nitrogen atom and optionally having a further nitrogen or oxygen atom, a heterocyclic ring having 3 to 5 carbons atoms; or wherein the substituents R' to R"' each represent ethylene residues, which form a bicyclic triethylenediamine skeleton with the quaternary nitrogen atom and a further tertiary nitrogen atom. If one or more of the substituents is a hydroxyalkyl group, then this substituent preferably has 2 to 4 carbon atoms and the hydroxyl group is preferably arranged in 2 position relative to the quaternary nitrogen atom. The hydroxyl-substituted substituent or substituents may also contain, apart from the hydroxyl substituents, other desired:, substituents, in particular $C_1$ to $C_4$ alkoxy substituents.

These last described catalysts are prepared in known manner by reacting tertiary amines with alkene oxides in an aqueous-alcohol medium (c.f. U.S. Pat. No. 3,995,997, column 2, lines 19–41). Suitable tertiary amines include trimethylamine, tributylamine, 2-dimethylaminoethanol, triethanolamine, dodecyldimethylamine, N,N-dimethylcyclohexylamine, N-methylpyrrolidine, N-methylmorpholine and 1,4-diazabicyclo-[2,2,2]-octane. Suitable alkene oxides include ethylene oxide, propylene oxide, 1,2-butylene oxide, styrene oxide or methoxy-, ethoxy- or phenoxypropylene oxide.

Especially preferred catalysts include N,N,N-trimethyl-N-(2-hydroxy-ethyl)ammonium hydroxide and N,N,N-trimethyl-N-(2hydroxypropyl)ammonium hydroxide. Also particularly suitable is the quaternary ammonium hydroxide of the preceding formula wherein R', R" and R"' are $CH_3$ and R"" is $-CH_2-C_6H_5$.

The trimerization catalysts are generally used in quantities of 0.005 to 5 wt. %, preferably 0.01 to 2 wt. %, based on the weight of the starting mixture used for the trimerization reaction. If a preferred catalyst such as N,N,N-trimethyl-N-(2-hydroxypropyl)ammonium hydroxide is used, then quantities of 0.05 to 1 wt. %, preferably 0.07 to 0.7 wt. %, based on the weight of the starting mixture, are generally sufficient. The catalysts may be used in pure form or in solution. Suitable solvents for the catalysts include those cited in the publications referred to above.

If hydroxyl compounds forming carbamic acid derivatives are used as co-catalysts, it is advantageous to use them simultaneously as a catalyst solvent. Suitable compounds for this purpose include methanol, ethanol, isopropanol, butanol, 2-ethylhexanol and glycols such as 1,2-ethanediol, 1,2-propanediol, 1,3- and 1,4-butanediol, 1,6- and 2,5-hexanediol and 2-ethyl-1,3-hexanediol.

The reaction temperature necessary for trimerization is 20° to 200° C., preferably 40° to 160° C. The trimerization reaction is preferably performed in the absence of solvents.

The trimerization may optionally be terminated at the desired degree of trimerization by adding a catalyst poison and/or by thermal deactivation of the catalyst. Suitable catalyst poisons for the particular trimerization catalysts are cited in the publications referred to above. In a preferred embodiment of the process according to the invention, the trimerization catalyst is not deactivated. Due to the comparatively low reactivity of the tertiary-bound isocyanate groups of starting component A), the reaction generally comes to a standstill on its own after trimerization of all of the primary and optionally secondary isocyanate groups present in the reaction mixture.

In addition, when the polyisocyanate mixtures according to the invention are produced, the type and amounts of the starting materials, and optionally the degree of trimerization, are selected such that a modified polyisocyanate or a modified polyisocyanate mixture is obtained which fulfills the requirements of parameters a) to f); the content of tertiary-bound isocyanaate groups in the modified polyisocyanate mixture is preferably 7 to 20 wt. %; the content of primary-bound and/or secondary-bound isocyanate groups is preferably below 0.5 wt. %; the average NCO functionality is preferably 2.1 to 5.0, more preferably 2.2 to 4.8; the urethane group content is preferably 3 1 to 25 wt. %; the isocyanurate group content is preferably 0 to 25 wt. %; the content of monomeric starting diisocyanates is less than 1%, preferably less than 0.5 wt. %; the content of ester groups is preferably 0 to 20 wt. % and the content of carbonate groups is preferably at 0 to 25 wt. % with the proviso that the total content of ester and carbonate groups is preferably 3% by weight. The modified polyisocyanate mixtures are solid below 40° C. and liquid above 125° C., preferably having a melting point or range determined by differential thermal analysis (DTA) of 40° to 110° C., more preferably of 50° to 100° C.

The polyisocyanate mixtures according to the invention generally fulfil these criteria, if the considerations stated above concerning the selection of starting materials, their amounts and the method of production are followed. The melting point or range may be increased by using branched polyhydroxyl compounds C) and optionally D) or reduced by using linear polyhydroxyl compounds. The NCO functionality may be increased by using higher functional polyhydroxyl compounds.

Functionality may also be adjusted in a desired manner by using differing quantities of diisocyanates B) having primary and/or secondary diisocyanate groups, in particular 1,6-diisocyanatohexane, in the trimerization reaction. Further, the isocyanurate content of the modified polyisocyanate mixture bears a direct influence upon its melting range, such that it is not only functionality, but also the melting range, which may be adjusted by the quantity of primarily bonded isocyanate groups present before the trimerization reaction.

The polyisocyanate mixtures according to the invention are valuable starting materials for the production of polyurethanes by the isocyanate polyaddition process. They are particularly suitable as crosslinking components in heat-curable two-component PUR powder coatings which do not contain blocking agents.

Suitable reaction partners for the polyisocyanate mixtures according to the invention are the known binders from powder coating technology which have groups which are reactive with isocyanates, such as hydroxyl, carboxyl, amino, thiol, urethane or urea groups, and are solid below 40° C. and liquid above 1300° C. Hydroxy-functional powder coating binders are preferred. The softening temperatures of these hydroxy-functional resins, determined by differential thermal analysis (DTA), are preferably 30° to 120° C., more preferably 35° to 110° C. Their hydroxyl numbers are generally 25 to 200, preferably 30 to 130, and their average molecular weight (which may be calculated from the functionality and hydroxyl content)is generally 400 to 10,000, preferably 1000 to 5000.

Such powder coating binders include polyesters, polyacrylates or polyurethanes containing hydroxyl groups and mixtures of these binders. These binders are described in the above-stated prior art publications, for example EP-A-0,045, 998 or EP-A-0,254,152.

To produce the ready-to-use powder coating, the polyisocyanate mixtures according to the invention are mixed with suitable powder coating binders, preferably hydroxy-functional powder coating binders, optionally with further auxiliaries and additives, such as catalysts, pigments, fillers or flow-control agents, and are combined into a homogeneous material in extruders or kneaders above the melting range of the individual components, for example, 70° to 130° C. The solid produced after the melt has cooled is then ground and the particles above the desired particle size, for example above 0.1 am, are removed by screening.

The polyisocyanate mixtures according to the invention and the hydroxy-functional binders are used in quantities sufficient to provide 0.6 to 1.2, preferably 0.8 to 1.0, isocyanate groups for each hydroxyl group.

The catalysts which may optionally also be used to accelerate curing are known from polyurethane chemistry and have previously been described for catalysis of the urethanization reaction. These catalysts may optionally be added in quantities of 0.01; to 5.0 wt. %, preferably 0.05 to 1.0 wt. %, based on the total weight of organic binder, i.e., the polyisocyanate mixtures according to the invention together with the powder coating binders, excluding any optional auxiliaries and additives.

The ready-to-spray powder coating may be applied to the substrate to be coated using customary powder application processes such as electrostatic powder spraying or fluidized bed coating. The coatings are cured at temperatures of 100° to 200° C., preferably 120° to 160° C., for example, for approximately 10 to %30 minutes. Even at low baking temperatures, glossy coatings having increased hardness and elasticity are obtained, which are characterized by exceptional solvent and chemical resistance and very good thermal color fastness.

Powder coatings produced with the polyisocyanate mixtures according to the invention exhibit increased resistance to light and weathering and are therefore particularly suited for external applications.

Any desired heat-resistant substrates, such as glass or metal substrates, may be coated according to the invention.

Apart from the described use as a powder coating hardener, the polyisocyanate mixtures according to the invention may also be dissolved in known lacquer solvents, such as esters, ketones or hydrocarbons, and optionally blocked with blocking agents, for use as a crosslinking component in solvent-based, one or two component polyurethane coating compositions.

The following examples further illustrate the invention. All parts and percentages, with the exception of the gloss values, are based on weight.

EXAMPLES

Production of starting component C)
Triol containing ester groups C1

2546 g of 1,1,1-trimethylolpropane (TMP) and 1431 g of ε-caprolactone were mixed together at room temperature under dry nitrogen, combined with 0.04 g of ortho-phosphoric acid and then heated to 160° C. for 5 hours. After cooling to room temperature, a colorless, liquid product was obtained having the following characteristics:

| | |
|---|---|
| viscosity (23° C.): | 3800 mPa · s |
| OH number: | 790 mg KOH/g |
| free caprolactone: | 0.2% |
| average molecular weight (calculated from OH number): | 213 |
| ester group content (calculated): | 13.9% |

Triol containing ester groups C2

590 g of 1,1,1-trimethylolpropane (TMP) and 1505 g of ε-caprolactone were mixed together at room temperature under dry nitrogen, combined with 0.02 g of ortho-phosphoric acid and then heated to 160° C. for 5 hours. After cooling to room temperature, a colorless, liquid product was obtained having the following characteristics:

| | |
|---|---|
| viscosity (23° C.): | 1400 mPa · s |
| OH number: | 341 mg KOH/g |
| free caprolactone: | 0.4% |
| average molecular weight (calculated from OH number): | 493 |

-continued

| | |
|---|---|
| ester group content (calculated): | 27.7% |

Diol containing ester groups C3

254 g of 1,6-hexanediol and 1146 g of ε-caprolactone were mixed together at room temperature under dry nitrogen, combined with 0.07 g of tin(11) octoate and then heated to 160° C. for 4 hours. After cooling to room, a colorless, liquid product was obtained having the following characteristics:

| | |
|---|---|
| viscosity (23° C.): | 330 mPa · s |
| OH number: | 172 mg KOH/g |
| free caprolactone: | 0.5% |
| average molecular weight (calculated from OH number): | 651 |
| ester group content (calculated): | 31.6% |

Triol containing ester groups C4

600 g of 1,1,1-trimethylolethane and 1140 g of ε-caprolactone were mixed together at room temperature under dry nitrogen, combined with 0.09 g of tin(11) octoate and then heated to 160° C. for 5 hours. After cooling to room temperature, a colorless, liquid product was obtained having the following characteristics:

| | |
|---|---|
| viscosity (23° C.): | 1920 mPa · s |
| OH number: | 468 mg KOH/g |
| free caprolactone: | 0.8% |
| average molecular weight (calculated from OH number): | 359 |
| ester group content (calculated): | 25.3% |

Example 1

1940 g (10.0 moles) of 1-isocyanato-1-methyl-4(3)-isocyanatomethylcyclohexane (IMCI) were heated to 80° C. under dry nitrogen. Then, within 2 to 3 hours, 851 g (4.0 moles) of the triol containing ester groups $C_1$ was stirred in such that the reaction temperature did not exceed 110° C. (NCO/OH equivalent ratio=1.7:1). On completion of addition, the mixture was stirred for a further 2 to 3 hours; at 100° to 110° C. until the theoretically calculated NCO content was reached. A polyisocyanate mixture according to the invention was obtained in the form of a colorless solid resin having an NCO content of 12.0%, a residual content of monomeric IMCI of 0.3% and a melting point of 65° to 68° C. The urethane group content was 25.3% and the ester group content 4.2%.

Example 2

776.0 g (4.0 moles) of IMCI were stirred into 190.4 g (0.39 moles) of the triol containing ester groups C2 at 60° C. within 30 minutes, wherein the internal temperature rose to 80° C. due to the exothermic reaction. Stirring was continued for 1 hour at 80° C. until an NCO content of 29.7% was reached. After cooling to 40° C., 67.2 g (0.4 moles) of hexamethylene diisocyanate (HDI) were added and the clear solution was degassed under a vacuum and aerated with $N_2$. For trimerization, 3 g of a catalyst solution (5% solution of trimethyl-benzyl-ammonium hydroxide in 1,3-butanediol) were added dropwise within 5 minutes at 40° C. The mixture was heated to 60° C. and the exothermic reaction was maintained at this temperature, initially by gentle cooling and later by heating, until after approx. 3 hours the NCO content had fallen below 21%. After approx. 2.5 hours, a further 1.5 g of the catalyst solution were added. The temperature was then gradually raised for another 2 hours to 80° to 90° C. After 1 hour at 90° C. another 1.5 g of catalyst solution was added and the temperature was raised to 110° C. towards the end of the reaction. On completion of the reaction, the melt was allowed to cool and a colorless solid resin according to the invention was obtained having an NCO content of 14.5%, a residual content of monomeric IMCI of 0.4%, a residual content of monomeric HDI of ≦0.03% and a melting point of 58 to 63° C. The urethane group content was 7.3%, the ester group content was 5.1% and the isocyanurate group content was 15.8%.

Example 3

1940 g (10 moles) of IMCI were reacted in a manner analogous to Example 1 with a mixture of 252 g (0.39 moles) of the diol containing ester groups C3 and 502 g (3.7 moles) of TMP. A polyisocyanate mixture according to the invention was obtained in the form of a colorless solid resin having an NCO content of 12.4%, a residual content of monomeric IMCI of 0.3% and a melting point of 86° to 90° C. The urethane group content was 26.3% and the ester group content was 2.9%.

Example 4

A mixture of 970 g (5 moles) of IMCI and 168 g (1 mole) of HDI was reacted in a manner analogous to Example 1 with a mixture of 557 g (1.6 moles) of the triol containing ester groups $C_4$ and 257 g (1.8 moles) of 1,4-cyclohexanedimethanol. A polyisocyanate mixture according to the invention was obtained in the form of a practically colorless solid resin having an NCO content of 8.0%, a residual content of IMCI of 0.3%, a residual content of monomeric HDI of 0.1% and a melting range of 82° to 87° C. The ester group content was 7.2% and the urethane group content was 24.9%.

Example 5

970 g (5 moles) of IMCI were reacted in a manner analogous to Example 1, with a mixture of 300 g (0.15 moles) of a polycarbonate diol having a molecular weight of 2000 and 255 g (1.9 moles) of TMP. The carbonate diol was prepared by reacting 1,6-hexanediol with diphenyl carbonate. A polyisocyanate mixture according to the invention was obtained in form of a colorless solid resin having an NCO content of 11.0%, a residual content of monomeric IMCI of 0.4% and a melting point of 64°–66° C. The content of urethane groups was 23.2%, of carbonate groups 7.7%.

Example 6 (Use)

75.6 parts by weight of a polyester containing hydroxyl groups (prepared from 66.6 parts by weight of terephthalic acid, 38.2 parts by weight of neopentyl glycol, 5.3 parts by weight of 1,6-hexanediol and 4.5 parts by weight of 1,1,1-trimethylolpropane) and having an OH number of 50 and a melting range (determined by differential thermal analysis) of 55° to 60° C., were thoroughly mixed with 23.4 parts by weight of the polyisocyanate mixture of Example 1 (NCO/OH equivalent ratio 1:1) and 1.0 part by weight of a commercial flow-control agent (Perenol F 30 P from Henkel, Dusseldorf). The powder coating was then homogenized using a Buss co-kneader, model PLK 46, at 150 rpm and a casing temperature of 40° C. in the inlet zone and at the shaft and 80° C. in the processing section, wherein material temperatures of 93° to 98° C. were reached. The solidified melt was ground and screened with an ACM 2 classifier mill (from Hosokawa Mikropul) with a 90 gm screen. The resulting powder was sprayed with an ESB spray cup gun at a high voltage of 70 kV onto a degreased steel sheets and cured for 30 minutes at both 140° C. and 160° C. to form a smooth, level, transparent coating.

At a film thickness of approx. 55 μm, the following coating properties were found:

|  | 140° C. | 160° C. |
|---|---|---|
| Gloss: (Gardner, reflection angle 60°) | 100% | 103% |
| Erichsen indentation: (DIN 53 156) | >9.0 mm | >9.0 mm |
| Gelation time: (DIN 55 990, part 8, section 5.1) | 212 sec/180° C. | |

The test demonstrates that a completely crosslinked, elastic coating was obtained after only 30 minutes at 140° C.

Example 2 (use)

A clear powder coating was formulated in accordance with the method described in Example 6 from 78.8 parts by weight of the polyester containing hydroxyl groups described in Example 5, 20.2 parts by weight of the polyisocyanate mixture of Example 2 (NGO/OH equivalent ratio 1:1) and 1.0 part by weight of a commercial flow-control agent (Peronol F 30 P from Henkel, Düsseldorf). The powder coating was sprayed onto a degreased steel sheet and baked for 30 minutes at 40° C. to a smooth, level, transparent coating.

At a film thickness of approx. 60 pm, the following coating properties were found:

| gloss: | 99% |
|---|---|
| Erichsen indentation: | >9.0 mm |
| Gelation time: | 152 sec/180° C. |

Example 8 (use)

A clear powder coating was formulated in accordance with the method described in Example 6 from 68.9 parts by weight of a polyacrylate containing hydroxyl groups (prepared from 37.0 pads by weight of methyl methacrylate, 24.0 parts by weight of n-butyl methacrylate, 18.9 parts by weight of styrene, 19.1 parts by weight of 2-hydroxyethyl methacrylate and 1.0 part by weight of acrylic acid) and having an OH number of 79 and a melting range (determined by differential thermal analysis) of 62° to 66° C., 30.1 parts by weight of the polyisocyanate mixture of Example 1 (NCO/OH equivalent ratio 1:1) and 1.0 part by weight of a commercial flow-control agent (Peronol F 30 P from Henkel, Düsseldorf). The powder coating was sprayed onto a degreased steel sheet and baked for 30 minutes at 1400° C. into a smooth, level, transparent coating.

At a film thickness of approx. 60 μm, the following coating properties were found:

| gloss: | 90% |
|---|---|
| acetone resistance: (50 double rubs with an acetone-soaked cotton wool swab) rating: 0 = film intact 1 = film surface softened 2 = film swollen down to substrate | 0 |
| gelation time: | 65 sec./180° C. |

The test demonstrates that a solvent resistant coating was obtained after only 30 minutes at 140° C.

Example 9 (use)

A clear powder coating was formed in accordance with the method described in Example 6 from 70.1 parts by weight of the polyacrylatae containing hydroxyl groups described in Example 8, 28.9 parts by weight of the polyisocyanate mixture of Example 2 (NCO/OH equivalent ratio 1:1) and 1.0 part by weigh of a commercial flow-control agent (Perenol F 30 P from Henkel, Düsseldorf). The powder coating was sprayed onto a degreased steel sheet and baked for 30 minutes at 140° C. into a smooth, level, transparent coating.

At a film thickness of approx. 55 μm, the following coating properties were found.

| gloss: | 93% |
|---|---|
| acetone resistance: | 0 |
| gelation time: | 44 sec/180° C. |

Example 10 (use)

A clear powder coating was formulated in accordance with the method described in Example 6 from 67.0 parts by weight of the polyacrylate resin containing hydroxyl groups of Example 8, 32.0 parts by weight of the polyisocyanate mixture of Example 2 (NCO/OH equivalent ratio 1:1) and 1.0 part by weight of the commercial flow-control agent of Example 9. The powder coating was sprayed onto degreased steel sheet and baked for 30 minutes at 140° C. into a smooth, level, transparent coating.

At a film thickness of approx. 55 μm, the following coating properties were found:

| gloss: | 94% |
|---|---|
| acetone resistance: | 0 |
| gelation time: | 61 sec/180° C. |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A mixture of polyisocyanates which is solid below 40° C. and liquid above 125° C. and which has a) an average isocyanate functionality of at least 2.1, b) a content of free isocyanate groups bonded to tertiary (cyclo)aliphatic carbon atoms (calculated as NCO; molecular weight=42) of 5 to 22 wt. %, c) a urethane group content (calculated as —NH—CO—O—; molecular weight=59) of 2 to 30 wt. %, d) an isocyanurate group content (calculated as $C_3N_3O_3$; molecular weight=126) of 0 to 30 wt. % and e) a carboxylic acid ester group content (calculated as —CO—O—; molecular weight=44) of 0 to 25 wt. % and/or f) a carbonate group content (calculated as —O—CO—O; molecular weight=60) of from 0 to 34 wt. % with the proviso that the total amount of ester groups e) and carbonate groups f) is at least 2 wt. %.

* * * * *